(12) United States Patent
Rowe

(10) Patent No.: US 11,796,527 B2
(45) Date of Patent: Oct. 24, 2023

(54) CARBON AND HYDROGEN ISOTOPE DETECTION AND REPORT WHILE DRILLING

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 112 days.

(21) Appl. No.: 17/487,213

(22) Filed: Sep. 28, 2021

(65) Prior Publication Data
US 2023/0098758 A1 Mar. 30, 2023

(51) Int. Cl.
*G01N 33/22* (2006.01)
*G01N 1/20* (2006.01)

(52) U.S. Cl.
CPC ............ *G01N 33/225* (2013.01); *G01N 1/20* (2013.01)

(58) Field of Classification Search
CPC ........ G01N 33/225; G01N 1/20; E21B 21/01; E21B 49/005; E21B 49/08
See application file for complete search history.

(56) References Cited

U.S. PATENT DOCUMENTS

| 7,124,030 B2 | 10/2006 | Ellis | |
| 10,371,691 B2 | 8/2019 | Strapoc et al. | |
| 10,711,605 B2 | 7/2020 | Rowe | |
| 2003/0160164 A1* | 8/2003 | Jones | ............ G01N 21/39 250/269.1 |
| 2017/0074094 A1* | 3/2017 | Rowe | ............ E21B 49/005 |
| 2017/0226851 A1 | 8/2017 | Hakami et al. | |
| 2019/0368345 A1 | 12/2019 | Rowe et al. | |
| 2020/0308963 A1* | 10/2020 | Dröge | ............ E21B 21/067 |

FOREIGN PATENT DOCUMENTS

| CN | 111095032 | 5/2020 |
| EP | 2824455 | 1/2015 |
| WO | 2019-143362 | 7/2019 |

OTHER PUBLICATIONS

Schlumberger, Isotope Logging, 2015.
Geolog Geoisotopes gas isotopic, Available at https://www.geolog.com/our-services/131/geoisotopes, Accesses Sep. 1, 2021.
Weatherford, Isotech Logging Device, 2015.
International Search Report and Written Opinion for Application No. PCT/US2021/054920, dated Jun. 20, 2022.

* cited by examiner

*Primary Examiner* — David J Bolduc
(74) *Attorney, Agent, or Firm* — Benjamin Ford; C. Tumey Law Group PLLC

(57) ABSTRACT

Systems and methods of the present disclosure generally relate to reporting carbon and hydrogen isotopic ratios during a wellbore operation. A method for detecting isotopic ratios during the wellbore operation, comprises receiving a fluid sample from a wellbore during the wellbore operation; passing the fluid sample to an analytical instrument operable to determine isotopic ratios in the fluid sample; outputting data comprising isotopic ratios for at least carbon and hydrogen; assigning a depth to the data; and transmitting the data based on isotopic ratios encountered during the wellbore operation.

20 Claims, 4 Drawing Sheets

CARBON AND HYDROGEN ISOTOPE DETECTION AND REPORT WHILE DRILLING

BACKGROUND

During drilling of a wellbore into a subterranean formation, formation fluid(s) may enter the wellbore and circulate with drilling fluid from the wellbore to the surface, and back into the wellbore. Detecting isotopes present in the formation fluids may indicate sources for each of the formation fluids, as well as thermal maturity for each of the formation fluids. However, detecting carbon isotope concentrations for a variety of chemical species without hydrogen isotope detection may only provide limited information regarding the formation fluids and the thermal maturity of the formation fluids.

BRIEF DESCRIPTION OF THE DRAWINGS

These drawings illustrate certain aspects of some examples of the present invention and should not be used to limit or define the invention.

DETAILED DESCRIPTION

Systems and methods of the present disclosure generally relate to wellbore operations and, more particularly, may relate to employing carbon and hydrogen isotope detection for a plurality of chemical species, along with formation gas composition detection, and lag corrections, to provide a more accurate assessment of the formation fluid(s) in place and the thermal maturity of the fluids.

The data acquired may be combined via a computer that may calculate and identify ratios of various chemical components. For example, at specified ratios of isotopes, with or without gas composition, an alert may be sent in real time to notify a designated party that a specific fluid has been encountered during drilling. The data may also be corrected for fractionation, recycling, and extraction bias.

The lag equations may be employed to account for depth at which isotopes are removed from the formation. In certain examples, a sampling device may continuously extract a fluid sample at a flow-in location for a wellbore such as at a suction line, for example or a flow-out location for the wellbore such as at a flow line, for example.

The sampling devices may extract sample fluids from drilling fluid in the form of a gas sample and/or a liquid sample. The flow-in sample or a flow-out sample may be sent to a sample conditioner, and pressure and flow controller. Contaminants may also be removed from the sample. In some examples, the sample may be mixed with a carrier gas. The sample may then flow to an analytical instrument (e.g., an isotope detection instrument) that may analyze the various chemical components (e.g., carbon and hydrogen isotopes).

The isotope detection instrument may include gas chromatography combustion isotope ratio mass spectrometer (GC-C-IRMS), gas chromatography combustion cavity ring-down spectrometer (GC-C-CRDS), gas chromatography combustion laser dispersion spectrometer (GC-C-LDS), gas chromatograph (GC), mass spectrometer (MS), or other suitable instruments. The sample may be tagged with a drilling depth based on the lag equations.

Outputs (e.g., isotope concentrations and ratios and gas compositions) from the isotope detection instrument may be transmitted to a computer with a program that includes pre-inputted specific ratios or inflections for compositional and/or isotopic ratios. For example, when specific ratios are encountered during drilling, an automated alert may be generated and sent to designated parties.

In particular examples, a minimum of methane, ethane, propane, argon, and/or hydrogen isotopic ratios are determined in addition to carbon. The isotopic ratios may be corrected for fractionation, recycling, or extraction bias.

Figure 1A:
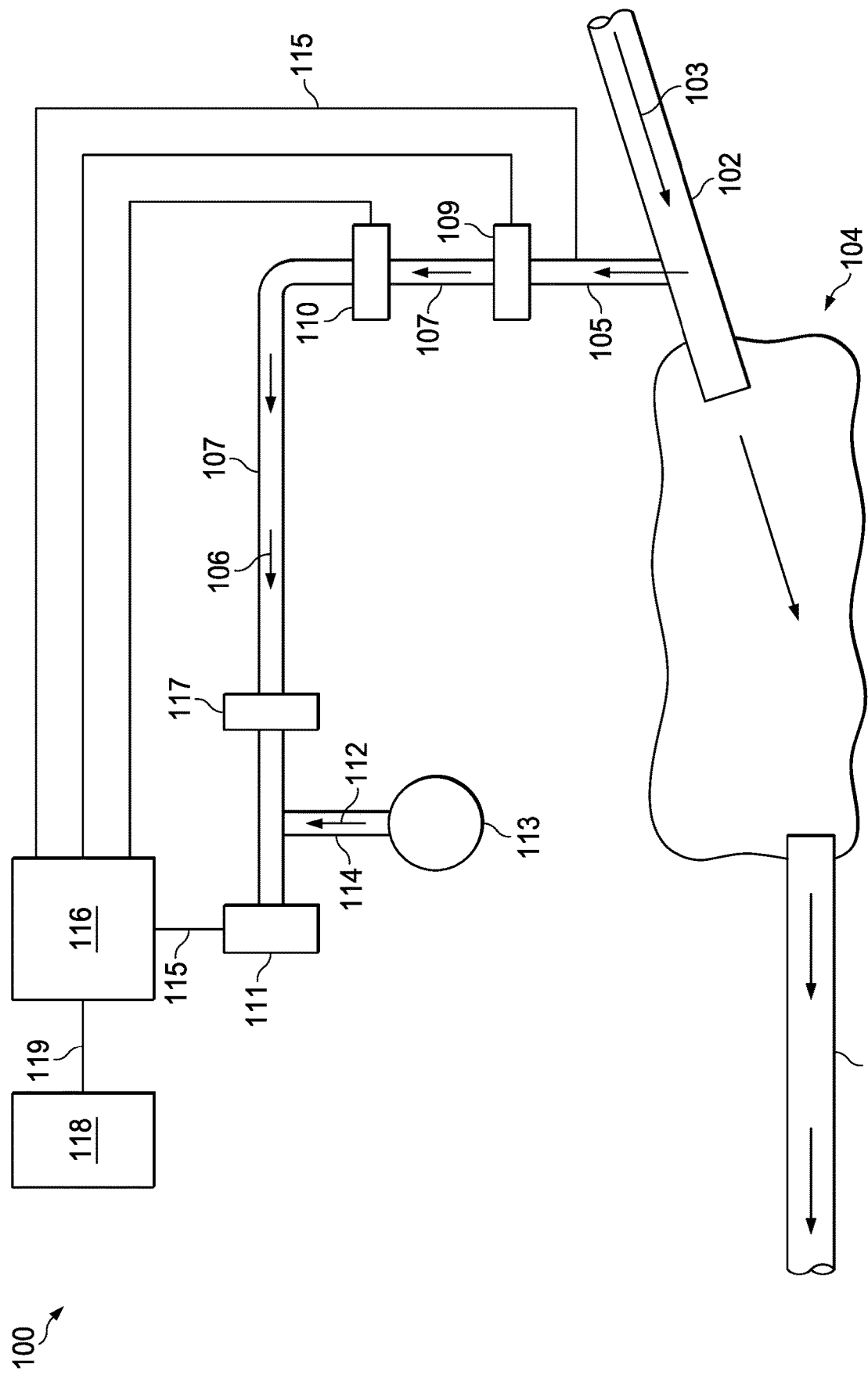
FIG. 1A illustrates a system disposed at a flow-out location from a wellbore, for real-time detection and reporting of at least carbon and hydrogen isotopic ratios, in accordance with particular examples of the present disclosure.

FIG. 1A illustrates a system 100 for employing carbon and hydrogen isotope detection, formation gas composition detection, and lag corrections, to determine formation fluid(s) in place and the thermal maturity of the fluids, in accordance with examples of the present disclosure. A flow line 102 may pass fluid 103 directly from a wellbore into a mud pit 104. A sampling device 105 may be in fluid communication with the flow line 102. The sampling device 105 may receive a sample 106 of the fluid 103 from the flow line 102.

Figure 1B:
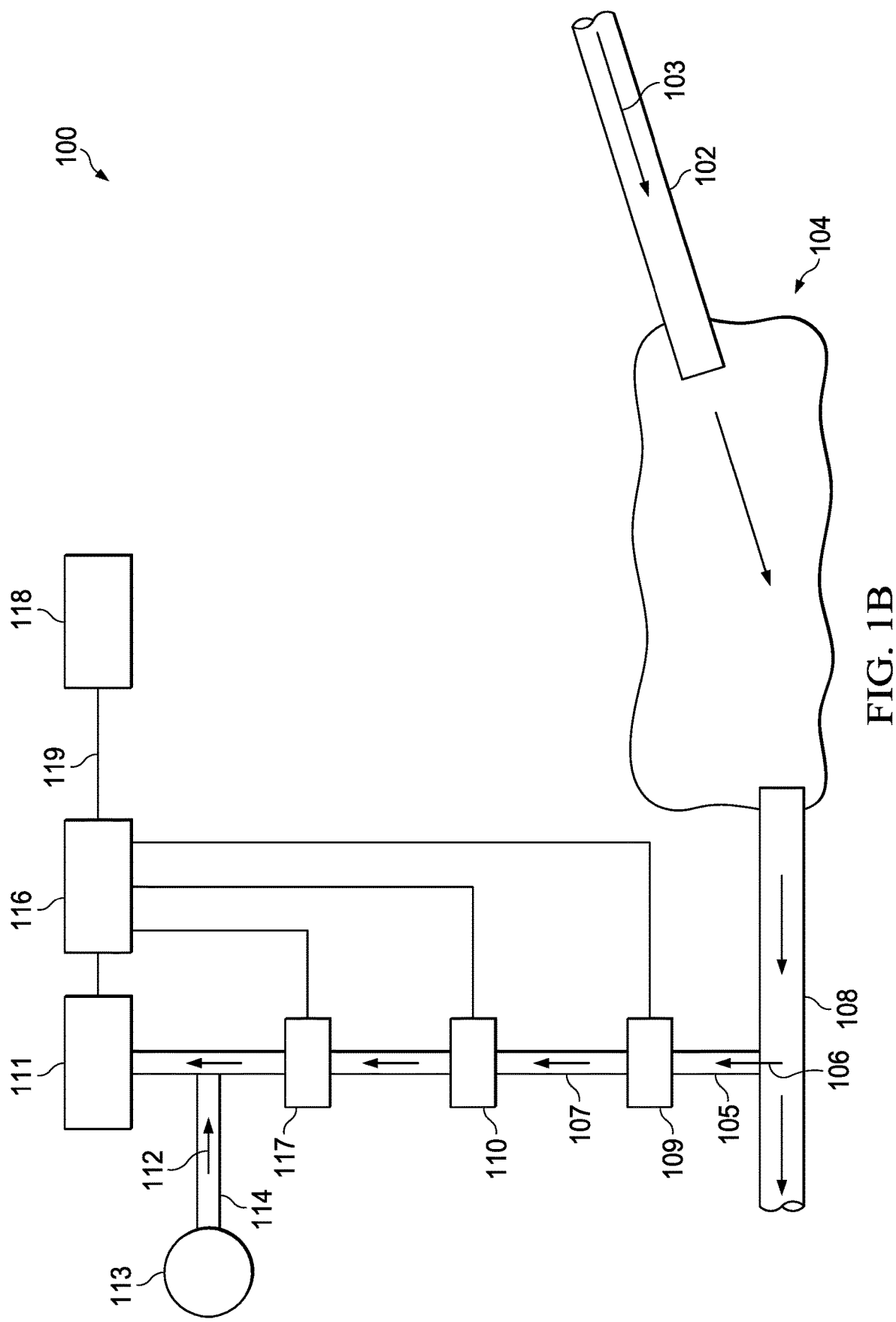
FIG. 1B illustrates the system disposed at a flow-in location for the wellbore, in accordance with particular examples of the present disclosure.

With additional reference to FIG. 1B, in some examples, the sampling device 105 may be disposed at a suction line 108 and may receive the sample 106 of the fluid 103 that passes through the suction line 108 from the mud pit 104.

The sampling device 105 may include any suitable sampling device for continuously receiving the sample 106 directly from the flow line 102 or the suction line 108, such as, for example, Quantitative Gas Measurement Extractor, Constant Volume Extractor, Constant Volume and Temperature Extractor.

The sample 106 may pass via conduits 107 to a sample conditioner 109, a pressure and flow controller 110, and then to an analytical instrument 111. The sample conditioner 109 may include, for example, a condensate removal jar, coalescing filter, sample dryer, and/or membrane filter.

In some examples, the sample 106 may be mixed with a carrier gas 112 from a source 113 (e.g., a tank, vessel, etc.). A conduit 114 may fluidly couple the source 113 to the conduit 107 to allow the carrier gas 112 to mix and carry the sample 106 into the analytical instrument 111. The analytical instrument 111 may include the GC-C-IRMS, GC-C-CRDS, GC-C-LDS, GC, MS, or other suitable instrument to determine isotopes and ratios and fluid compositions, as previously noted.

The sampling device 105, the sample conditioner 109, the pressure and flow controller 110, and the analytical instrument 111 may be in communication (e.g., wired or wireless communication paths 115) with a computer 116 that may process data from sampling device 105, the sample conditioner 109, the pressure and flow controller 110, and the analytical instrument 111.

In some examples, a physical separation device 117 may be disposed upstream to the analytical instrument(s) to separate molecules based on molecular size or functional groups. The separation device 117 may include a gas chromatography column. The samples may also be oxidized before isotope analysis to simplify the analysis. The samples may be oxidized with a flame or a furnace with a catalyst.

The computer 116 may operate the system 100 and may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The computer 116 may be any processor-driven device, such as, but not limited to, a personal computer, laptop computer, smartphone, tablet, handheld computer, dedicated processing device, and/or an array of computing devices. In addition to having a processor, the computer 116 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases. The computer 116 may also include display devices such as a monitor featuring an operating system, media browser, and the ability to run one or more software applications. Additionally, the computer 116 may include non-transitory computer-readable media. Non-transitory computer-readable media may include any instrumentality or aggregation of instrumentalities that may retain data and/or instructions for a period of time.

The computer 116 may utilize a lag equation(s) to tag the sample 106 with a drilling depth. An example of a lag equation may be defined by Equation (I):

$$\text{Lag} = \text{Wellbore Annular Volume/Pump Output Rate} \quad \text{Eq. (1)}$$

The computer 116 may also be operable via a program, for example, to store thresholds such as pre-inputted specific ratios or inflections for compositional and/or isotopic ratios. Output of the analytical instrument 114 may be received by the computer 116 and upon satisfying the thresholds (e.g., the specific ratios are encountered in a formation), an automated alert may be generated and transmitted to designated parties 118 via a communication path 119. In particular examples, a minimum of methane, ethane, propane, argon, and/or hydrogen isotopic ratios may be determined in addition to carbon. The isotopic ratios may be corrected for fractionation, recycling, or extraction bias.

Figure 2:
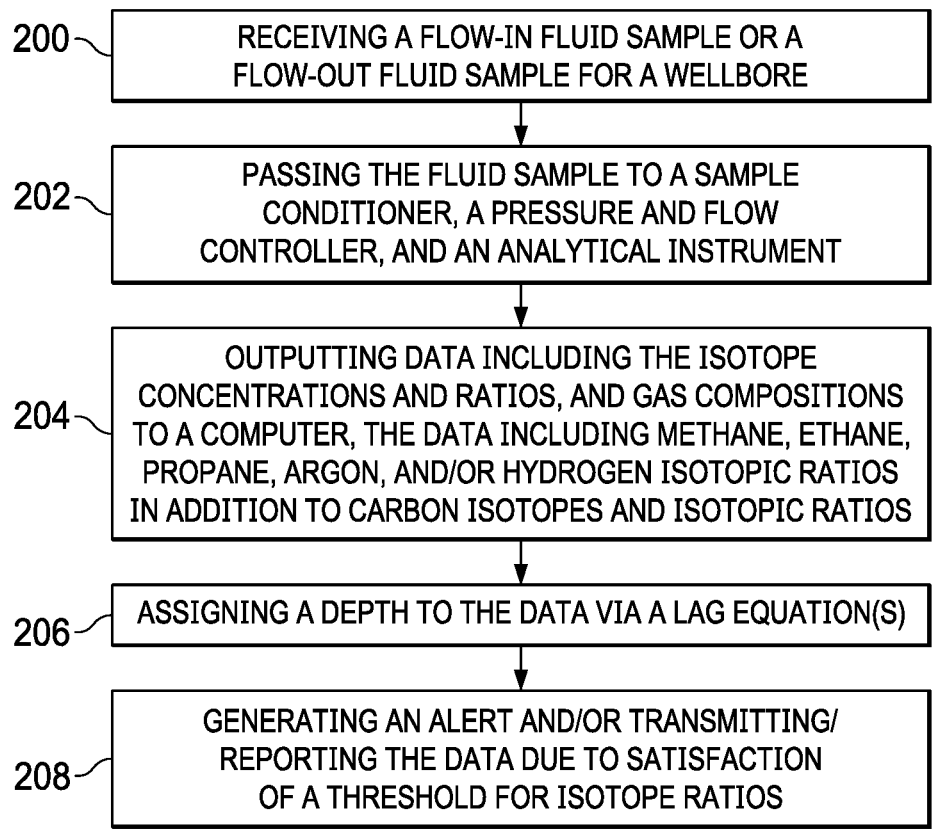
FIG. 2 illustrates an exemplary method to determine and report at least carbon and hydrogen isotopic ratios during a wellbore operation, in accordance with particular examples of the present disclosure.

FIG. 2 illustrates an exemplary method to determine a corrected isotope ratio during wellbore operations, in accordance with particular examples of the present disclosure. At step 200, a flow-in fluid sample or a flow-out fluid sample may be extracted from a flow line or a suction line for a wellbore, respectively, as shown on FIGS. 1A and 1B, for example. The extraction of fluid samples may occur continuously with the sampling device. The fluid samples may include gas and/or liquid.

At step 202, the extracted sample may be extracted with a sampling device and pass through a sample conditioner, a pressure and flow controller, and analytical instrument for analysis with a computer, as shown on FIGS. 1A and 1B, for example.

In some examples, the carrier gas may be employed to move the sample for analysis. As noted above, the analytical instrument may include the GC-C-IRMS, GC-C-CRDS, GC-C-LDS, GC, MS, or other suitable instrument to determine isotopes, and isotopic ratios, and fluid compositions.

At step 204, data (e.g., isotope concentrations, isotopic ratios, and gas compositions) acquired with the analytical instrument may be transmitted to a computer with a program that includes pre-inputted specific ratios or inflections for compositional and/or isotopic ratios. As noted earlier, a minimum of methane, ethane, propane, argon, and/or hydrogen isotopes and isotopic ratios may be determined in addition to carbon isotopes and isotopic ratios.

At step, 206 the data may be tagged, via a computer, with a drilling depth via the lag equation(s) and in some examples, the isotopic ratios may be corrected for fractionation, recycling, and/or extraction bias.

At step 208, an automated alert may be generated and/or transmitted to designated parties 118 via the computer. For example, when specific ratios are encountered during drilling, an automated alert may be generated and/or sent to the designated parties due to satisfaction of a threshold for isotope ratios.

Figure 3:
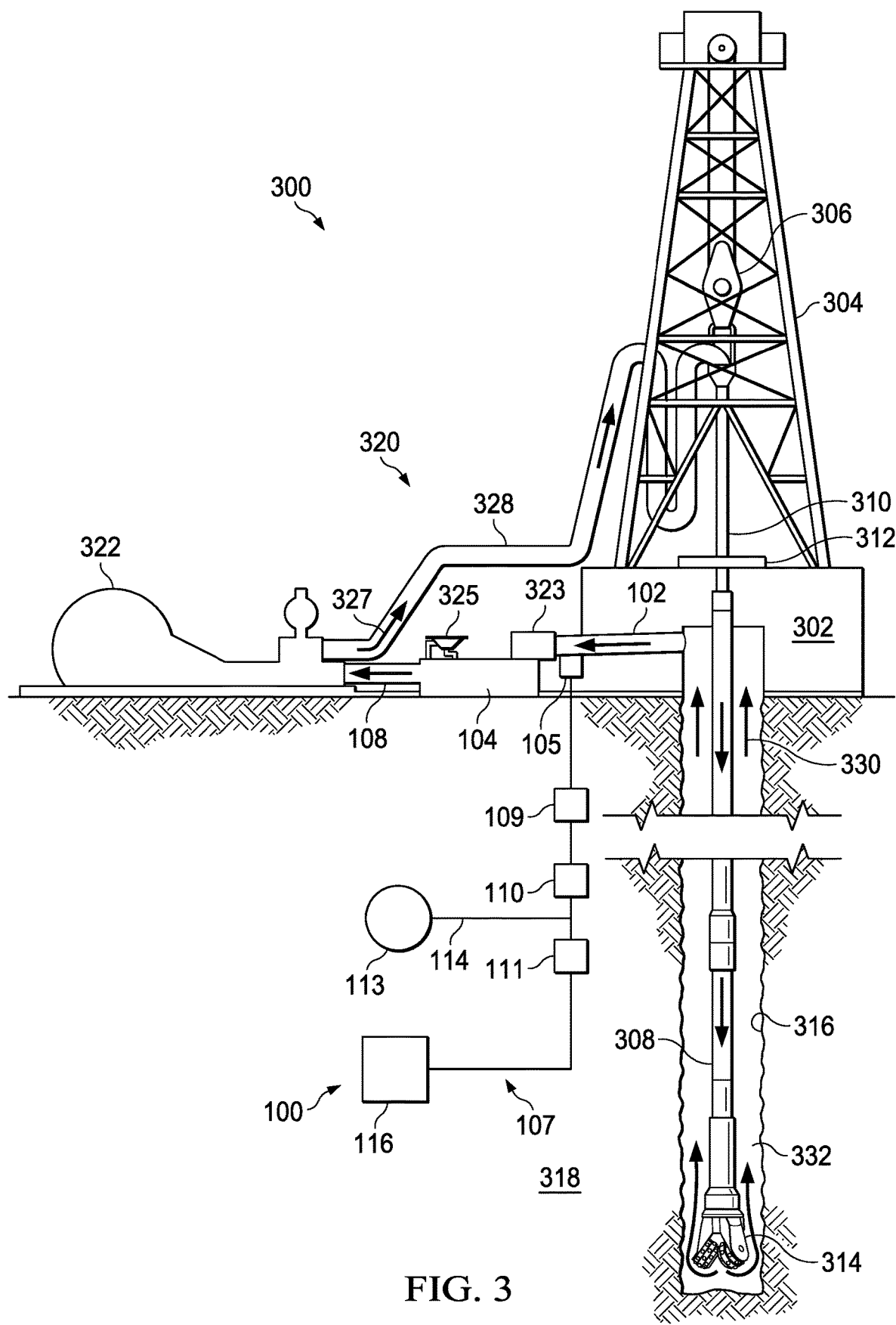
FIG. 3 is a schematic diagram of an exemplary drilling system including the system for real-time detection and reporting of at least carbon and hydrogen isotopic ratios, in accordance with particular examples of the present disclosure.

FIG. 3 illustrates a drilling system 300 including the system 100 and the workflow of FIG. 2 in accordance with particular examples of the present disclosure. It should be noted that while FIG. 3 depicts a land-based drilling system, those skilled in the art will readily recognize that the principles described herein are equally applicable to subsea drilling operations that employ floating or sea-based platforms and/or rigs, without departing from the scope of the present disclosure.

Additionally, although system 100 is illustrated as being directly coupled to the flow line 102, it should be noted that the system 100 may be coupled to any flow-in or flow-out location in relation to a wellbore.

As illustrated, the drilling system 300 may include a drilling platform 302 that supports a derrick 304 having a traveling block 306 for raising and lowering a drill string 308. The drill string 308 may include, but is not limited to, drill pipe and coiled tubing, as generally known to those skilled in the art. A top drive or kelly 310 may support the drill string 308. The drill string 308 may be lowered through a rotary table 312, in some examples. A drill bit 314 may be attached to the distal end of the drill string 308 and may be driven either by a downhole motor and/or via rotation of the drill string 308 from the well surface. Without limitation, the drill bit 314 may include, roller cone bits, PDC bits, natural diamond bits, any hole openers, reamers, coring bits, and the like. As the drill bit 314 rotates, it may create a wellbore 316 that penetrates a subterranean formation 318.

The drilling system 300 may further include a fluid monitoring and handling system 320 comprising component parts such as a mud pump 322, a solids control device 323, a mixing hopper 325 and the mud pit 104. The mud pump 322 may include any conduits, pipelines, trucks, tubulars, and/or pipes used to convey clean drilling fluid 327 downhole. The mud pump 322 may also include any pumps, compressors, or motors (e.g., surface or downhole) used to move the clean drilling fluid 327, as well as any valves or related joints used to regulate the pressure or flowrate of the clean drilling fluid 327, and any sensors (e.g., pressure, temperature, flow rate), gauges, or combinations thereof, for example. The mud pump 322 may circulate the clean drilling fluid 327 from the mud pit 104 via the suction line 108.

The mud pump 322 may circulate the clean drilling fluid 327 through a feed pipe 328 and to the top drive or kelly 310, which may convey the clean drilling fluid 327 downhole through the interior of the drill string 308 and through one or more orifices in the drill bit 314. The now circulated drilling fluid 330 may then be circulated back to the surface via an annulus 332 defined between the drill string 308 and the walls of the wellbore 316. At the surface, the circulated drilling fluid 330 may be conveyed to the solids control device 323 via the flow line 102. The solids control device 323 may include one or more of a shaker (e.g., shale shaker), a centrifuge, a hydro-cyclone, a separator (including magnetic and electrical separators), a de-silter, a de-sander, a separator, a filter (e.g., diatomaceous earth filters), a heat exchanger, and any fluid reclamation equipment. The solids control device 323 may remove and separate recovered solids from the circulated drilling fluid 330. After passing through the solids control device 323, the clean drilling fluid 327 may move into the mud pit 104.

The sampling device 105 may continuously sample/receive fluid samples. The fluid samples may pass through the sample conditioner 109, the pressure and flow controller 110, and the analytical instrument 111.

In some examples, the sample 106 may be mixed with a carrier gas from a source 113. A conduit 114 may fluidly couple the source 113 to the conduit 107 to allow the carrier gas to mix and carry the sample 106 into the analytical instrument 111.

As noted previously, the analytical instrument 111 may include the GC-C-IRMS, GC-C-CRDS, GC-C-LDS, GC, MS, or other suitable instrument to determine isotopes and ratios, and fluid compositions. At least methane, ethane, propane, argon, and/or hydrogen isotopes and isotopic ratios may be determined in addition to carbon isotopes and isotopic ratios.

The computer 116 may receive the isotope/isotope ratio information from the analytical instrument 111 and may utilize the lag equation to tag a depth to the isotope information and in some examples, the isotopic ratios may be corrected for fractionation, recycling, and/or extraction bias.

In some examples, an automated alert or report may be generated and/or transmitted to the designated parties 118 via the computer 116 when specific isotopic ratios are encountered during drilling.

Accordingly, the systems and methods of the present disclosure may provide at least carbon and hydrogen isotopic ratio detection reports while drilling. The systems and methods may include any of the various features disclosed herein, including one or more of the following statements.

Statement 1. A method for detecting isotopic ratios during a wellbore operation, comprising: receiving a fluid sample from a wellbore during the wellbore operation; passing the fluid sample to an analytical instrument operable to determine isotopic ratios in the fluid sample; outputting data comprising isotopic ratios for at least carbon and hydrogen; assigning a depth to the data; and transmitting the data based on isotopic ratios encountered during the wellbore operation.

Statement 2. The method of the statement 1, further comprising passing the sample through a sample conditioner.

Statement 3. The method of the statement 2, further comprising passing the sample through a flow and pressure controller.

Statement 4. The method of any of the preceding statements, further comprising moving the sample with a carrier gas into the analytical instrument.

Statement 5. The method of any of the preceding statements, further comprising receiving the flow-in fluid sample from a flow line of a drilling system.

Statement 6. The method of any of the preceding statements, further comprising receiving the flow-out fluid sample from a suction line of a drilling system.

Statement 7. The method of any of the preceding statements, further comprising generating an alert based on the isotopic ratios encountered during the wellbore operation.

Statement 8. The method of any of the preceding statements, further comprising outputting data that includes methane, ethane, propane, and/or argon isotopic ratios.

Statement 9. The method of any of the preceding statements, further comprising continuously sampling the flow-in fluid sample.

Statement 10. The method of any of the preceding statements, further comprising continuously sampling the flow-out fluid sample.

Statement 11. A system for detecting isotopic ratios during a wellbore operation, comprising: an analytical instrument operable to determine isotopic ratios in a wellbore fluid; a fluid sampling device operable to sample fluid from a wellbore; and a computer operable to: receive data comprising isotopic ratios for at least carbon and hydrogen, from the analytical instrument; assign a depth to the data; and transmit the data based on isotopic ratios encountered during the wellbore operation.

Statement 12. The system of any of the statements 11, further comprising a flow and pressure controller disposed upstream to the analytical instrument.

Statement 13. The system of the statement 11 or the statement 12, further comprising a sample conditioner disposed upstream to the analytical instrument.

Statement 14. The system of any of the statements 11-13, further comprising a source that includes a carrier gas.

Statement 15. The system of any of the statements 11-14, wherein the computer is further operable to generate an alert based on the isotopic ratios encountered during the wellbore operation.

Statement 16. The system of any of the statements 11-15, wherein the data further includes methane, ethane, propane, and/or argon isotopic ratios.

Statement 17. The system of any of the statements 11-16, wherein the second sampling device is disposed at a suction line of a drilling system.

Statement 18. The system of any of the statements 11-17, wherein the first sampling device is disposed at a flow line of a drilling system.

Statement 19. The system of any of the statements 11-18, wherein the first sampling device is operable to continuously sample the wellbore fluid.

Statement 20. The system of any of the statements 11-19, wherein the second sampling device is operable to continuously sample the wellbore fluid.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method for determining formation fluids in place and the thermal maturity of the fluids during a wellbore operation, comprising:
   receiving a fluid sample from a wellbore during the wellbore operation;
   passing the fluid sample to an analytical instrument operable to determine isotopic ratios and gas compositions in the fluid sample;
   outputting data comprising an isotopic ratio for carbon;
   outputting data comprising an isotopic ratio for hydrogen;
   outputting data comprising gas compositions;
   assigning a depth to the data;
   transmitting the data based on isotopic ratios and gas compositions encountered during the wellbore operation; and
   providing an assessment of the formation fluids in place and the thermal maturity of the fluids.

2. The method of claim 1, further comprising passing the sample through a sample conditioner.

3. The method of claim 1, further comprising passing the sample through a flow and pressure controller.

4. The method of claim 1, further comprising moving the sample with a carrier gas into the analytical instrument.

5. The method of claim 1, further comprising receiving a flow-in fluid sample from a flow line of a drilling system.

6. The method of claim 1, further comprising receiving a flow-out fluid sample from a suction line of a drilling system.

7. The method of claim 1, further comprising generating an alert based on the isotopic ratios encountered during the wellbore operation.

8. The method of claim 1, further comprising outputting data that includes methane, ethane, propane, and/or argon isotopic ratios.

9. The method of claim 1, further comprising continuously sampling a flow-in fluid sample.

10. The method of claim 1, further comprising continuously sampling a flow-out fluid sample.

11. A system for determining formation fluids in place and the thermal maturity of the fluids during a wellbore operation, comprising:
    an analytical instrument operable to determine isotopic ratios and gas compositions in a wellbore fluid;
    a fluid sampling device operable to sample fluid from a wellbore; and
    a computer operable to:
      receive data comprising an isotopic ratio for carbon, from the analytical instrument;
      receive data comprising an isotopic ratio for hydrogen, from the analytical instrument;
      receive data comprising gas compositions;
      assign a depth to the data;
      transmit the data based on isotopic ratios and gas compositions encountered during the wellbore operation; and
      provide an assessment of the formation fluids in place and the thermal maturity of the fluids.

12. The system of claim 11, further comprising a flow and pressure controller disposed upstream to the analytical instrument.

13. The system of claim 11, further comprising a sample conditioner disposed upstream to the analytical instrument.

14. The system of claim 11, further comprising a source that includes a carrier gas.

15. The system of claim 11, wherein the computer is further operable to generate an alert based on the isotopic ratios encountered during the wellbore operation.

16. The system of claim 11, wherein the data further includes methane, ethane, propane, and/or argon isotopic ratios.

17. The system of claim 11, wherein the sampling device is disposed at a suction line of a drilling system.

18. The system of claim 11, wherein the sampling device is disposed at a flow line of a drilling system.

19. The system of claim 11, wherein the sampling device is operable to continuously sample the fluid.

20. The system of claim 11, wherein the sampling device is disposed at a flow line of a drilling system and is operable to continuously sample the fluid.

* * * * *